United States Patent [19]

Horne et al.

[11] 4,451,466

[45] May 29, 1984

[54] USE OF PYRROLOQUINAZOLINEDIAMINES AS PESTICIDES

[75] Inventors: Charles A. Horne; Stephen A. Salvo; Kurt G. R. Sundelin, all of Modesto, Calif.; Steven A. Roman, Fulshear, Tex.

[73] Assignee: Shell Oil Company, Houston, Tex.

[21] Appl. No.: 394,968

[22] Filed: Jul. 2, 1982

[51] Int. Cl.$^3$ .................... A01N 43/54; A01N 43/84; A01N 43/86; A01N 43/88

[52] U.S. Cl. .............................. 424/251; 424/248.53; 424/248.54; 424/248.55

[58] Field of Search .............. 424/251, 248.53, 248.54, 424/248.55

[56] References Cited

U.S. PATENT DOCUMENTS

| | | | |
|---|---|---|---|
| 4,118,561 | 10/1978 | Ledig | 424/251 |
| 4,208,520 | 6/1980 | Ledig et al. | 424/251 |
| 4,288,595 | 9/1981 | Ledig et al. | 424/251 |

*Primary Examiner*—Albert T. Meyers
*Assistant Examiner*—John M. Kilcoyne

[57] ABSTRACT

Certain 7H-pyrrolo[3,2-f]quinazoline-1,3-diamines are useful as pesticides.

1 Claim, No Drawings

USE OF PYRROLOQUINAZOLINEDIAMINES AS PESTICIDES

DESCRIPTION OF THE INVENTION

It has been found that useful pesticidal properties are possessed by 7H-pyrrolo[3,2-f]quinazoline-1,3-diamines of the formula

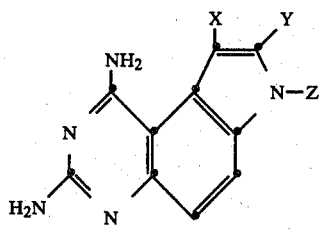

and acid addition salts thereof, wherein
(A) X is hydrogen, Y is hydrogen, halogen, alkyl of from one to six carbon atoms, or phenyl, and Z is one of
(i) hydrogen;
(ii) straight-chain or branched-chain alkyl of up to eight carbon atoms;
(iii) a moiety R— or R—A—, wherein A is alkylene of from one to three carbon atoms with from one to two carbon atoms in the linking chain, and R is one of
(a) phenyl; naphthalenyl;
(b) phenyl substituted by alkanoyl of from two to six carbon atoms, aminocarbonyl, alkoxycarbonyl of from two to six carbon atoms, alkylsulfonyl of from one to three carbon atoms, or by from one to four substituents selected from halogen; nitro; amino, monoalkylamino or dialkylamino in which such alkyl contains from one to four carbon atoms; cyano; trifluoromethyl, pentafluoroethyl; trifluoromethoxy; or alkyl, alkoxy and alkylthio of from one to four carbon atoms each;
(c) pyridinyl, thienyl, thiazolyl, isoxazolyl, quinolyl, pyrimidinyl, pyrazinyl, quinoxalinyl, or any of these substituted by from one to three substituents selected from halogen, nitro, trifluoromethyl, phenyl, and alkyl of from one to four carbon atoms; 1-benzo[b]thienyl;
(iv) cycloalkyl of from three to six carbon atoms;
(v) phenylsulfonyl or phenylsulfonyl substituted by from one to three substituents selected from halogen, and alkyl of from one to four carbon atoms;
(B) X and Y together represent an alkylene moiety of from one to four carbon atoms, which may be substituted by one to three substituents selected from halogen, alkyl, alkoxy and alkylthio of from one to six carbon atoms, and Z is as defined in (A).

In these compounds, "halogen" denotes chlorine, fluorine or bromine, and preferably "—A—" is methylene (—CH$_2$—), while any alkyl moiety bonded to a ring, or present in a moiety bonded to a ring, is methyl.

Suitable acid addition salts are those which are not phytotoxic, and include the salts of such acids as hydrochloric acid, sulfuric acid, hydrobromic acid, nitric acid, maleic acid, benzoic acid, acetic acid, pamoic acid, methanesulfonic acid, and the like.

Compounds of Formula I have been found to be intrinsically toxic to insects, and can act as contact insecticides if applied in a form which enables penetration of the compound into the insect. However, because of their physical properties, it is difficult to use those compounds in that fashion. The compounds are solids at ordinary conditions, and have only very limited solubility in common solvents. Thus, the pest is not harmed by merely contacting a compound of Formula I—as by walking upon a treated leaf, or even, in the case of some formulations, being contacted with a spray or dust containing the compound, because an effective dosage of the compound does not penetrate into the insect.

Accordingly, the compounds of Formula I are primarily of interest for controlling chewing pests, the compound being incorporated on or into the food, or other material, that the pest to be controlled will ingest. As contemplated in this invention, a chewing pest is an arthropod—in mature, immature or larval, maggot or grub stage of development—that ingests its food by biting and chewing and/or that ingests other material by biting or chewing when adapting its environment to its needs—as when building a nest, constructing a tunnel or burrow, or the like. For the most part, the contemplated pests are insects and arthropods closely related thereto, including such crustaceans as the isopods (pillbugs, sowbugs) and teredos, chilopods such as the centipedes, diplopods such as the millipedes, and symphylids.

Compounds of Formula I have been found to be highly toxic with respect to pests, yet to have relatively little toxicity with respect to mammals.

As a consequence of these characteristics of the compounds of Formula I, the method of the invention is adapted to the following general areas of pest control:
(a) protection of plants from insects that feed upon their foliage, such as the larval forms of a variety of different insect species, cutworms, grasshoppers and crickets;
(b) protection of wooden and plastic building materials from such insect and related pests as subterranean termites, drywood termites, Formosan termites, black carpenter ants, powder post beetles, marine borers, wood borers, and teredos;
(c) control of household and yard pests, such as cockroaches, ants, silverfish, carpet beetles, clothes moths, houseflies and mosquitoes (larvae);
(d) control of stored product pests such as flour beetles, granary and rice weevils, grain beetles, pea and bean weevils, flour, grain and meal moths and Khapra beetles;
(e) fecal fly control.

The activity of compounds of Formula I for controlling pests that feed upon the foliage of plants was established in tests wherein larvae of the corn earworm (cotton bollworm) (*Heliothis zea*) were allowed to feed on the foliage of plants which had been sprayed with a liquid formulation (10% dimethyl sulfoxide/acetone) containing the compound to be tested, and in tests wherein the compound to be tested was mixed with the food supplied to larvae of the corn earworm, and larvae of the beet armyworm (*Spodoptera exigua*). Table I lists the species of the genus defined by Formula I that were found to be active with respect to the larvae of one or both of these species of insects. (The compounds are defined in terms of the symbols in Formula I.)

TABLE I

| Compound No. | X | Y | Z |
|---|---|---|---|
| 1 | H | H | hydrogen |
| 2 | H | H | 3-methyl-2-butenyl |
| 3 | H | H | n-heptyl |
| 4 | H | H | phenylmethyl (as the hydrochloride salt) |
| 5 | H | H | phenylmethyl (as the free base) |
| 6 | H | H | 3-phenylpropyl |
| 7 | H | H | cyclohexylmethyl |
| 8 | H | H | 2-methoxyphenylmethyl |
| 9 | H | H | 2,5-dimethoxyphenylmethyl |
| 10 | H | H | 4-methoxyphenylmethyl |
| 11 | H | H | 3,5-dimethoxyphenylmethyl |
| 12 | H | H | 3,4,5-trimethoxyphenylmethyl |
| 13 | H | H | 4-ethoxyphenylmethyl |
| 14 | H | H | 2-methylphenylmethyl |
| 15 | H | H | 3-methylphenylmethyl |
| 16 | H | H | 2,5-dimethylphenylmethyl |
| 17 | H | H | 2,6-dimethylphenylmethyl |
| 18 | H | H | 3,4-dimethylphenylmethyl |
| 19 | H | H | 2,3,5,6-tetramethylphenylmethyl |
| 20 | H | H | 2,4,6-trimethylphenylmethyl |
| 21 | H | H | 4-methylphenylsulfonyl |
| 22 | H | H | 3-acetylphenylmethyl |
| 23 | H | H | 4-acetylphenylmethyl |
| 24 | H | H | 4-ethoxycarbonylphenylmethyl |
| 25 | H | H | 3-methoxycarbonylphenylmethyl |
| 26 | H | H | 3-(1-methylethyl)phenylmethyl |
| 27 | H | H | 4-trifluoromethylphenylmethyl |
| 28 | H | H | 3-trifluoromethylphenylmethyl |
| 29 | H | H | 4-trifluoromethoxyphenylmethyl |
| 30 | H | H | 4-(1,1-dimethylethyl)phenylmethyl |
| 31 | H | H | 4-(1,1-dimethylethyl)phenylsulfonyl |
| 32 | H | H | 4-(methylthio)phenylmethyl |
| 33 | H | H | 4-methylsulfonylphenylmethyl |
| 34 | H | H | 4-(1-methylethyl)phenylmethyl |
| 35 | H | H | 4-(1-methylbutoxycarbonyl)phenylmethyl |
| 36 | H | H | 2-chlorophenylmethyl |
| 37 | H | H | 3-chlorophenylmethyl |
| 38 | H | H | 2,4-dichlorophenylmethyl |
| 39 | H | H | 3,4-dichlorophenylmethyl |
| 40 | H | H | 2,6-dichlorophenylmethyl |
| 41 | H | H | 4-fluorophenylmethyl |
| 42 | H | H | 4-chlorophenylsulfonyl |
| 43 | H | H | 3,4-dichlorophenylsulfonyl |
| 44 | H | H | 2-pyridinylmethyl |
| 45 | H | H | 4-pyridinylmethyl |
| 46 | H | H | 4-cyanophenylmethyl |
| 47 | H | H | 3-cyanophenylmethyl |
| 48 | H | H | 3-aminophenylmethyl |
| 49 | H | H | 3-nitrophenylmethyl |
| 50 | H | H | 3-thienylmethyl |
| 51 | H | H | 2-thienylmethyl |
| 52 | H | H | 1-benzo[b]thien-3-ylmethyl |
| 53 | H | H | 4-thiazolylmethyl |
| 54 | H | H | 3,5-dimethyl-4-isoxazolylmethyl |
| 55 | H | H | 1-naphthalenylmethyl |
| 56 | H | H | 2-methyl-1-naphthalenylmethyl |
| 57 | H | H | 8-quinolinylmethyl |
| 58 | H | H | 2-quinolinylmethyl |
| 59 | H | H | 1-bromo-2-naphthalenylmethyl |
| 60 | H | H | 2-acetylphenyl |
| 61 | H | H | 4-acetylphenyl |
| 62 | H | H | 4-methylsulfonylphenyl |
| 63 | H | H | 4-aminocarbonylphenyl |
| 64 | H | H | 2-nitrophenyl |
| 65 | H | H | 4-nitrophenyl |
| 66 | H | H | 3-methyl-4-nitrophenyl |
| 67 | H | H | 2-cyano-4-nitrophenyl |
| 68 | H | H | 4-cyanophenyl |
| 69 | H | H | 4-nitro-2-trifluoromethylphenyl |
| 70 | H | H | 4-trifluoromethylphenyl |
| 71 | H | H | 4-aminophenyl |
| 72 | H | H | 2-pyridinyl |
| 73 | H | H | 4-pyridinyl |
| 74 | H | H | 5-nitro-2-pyridinyl |
| 75 | H | H | 2-pyrimidinyl |
| 76 | H | H | pyrazinyl |
| 77 | H | H | 4-methyl-2-pyridinyl |
| 78 | H | H | 2-thiazolyl |
| 79 | H | H | 2-benzothiazolyl |
| 80 | H | H | 2-quinolinyl |
| 81 | H | H | 4-quinolinyl |
| 82 | H | H | 2-methyl-4-quinolinyl |
| 83 | H | H | 7-trifluoromethyl-4-quinolinyl |
| 84 | H | H | 2-phenyl-5-quinolinyl |
| 85 | H | H | 7-chloro-4-quinolinyl |
| 86 | H | H | 3-methyl-2-quinoxalinyl |
| 87 | H | Cl | Phenylmethyl |
| 88 | H | methyl | hydrogen |
| 89 | H | methyl | phenylmethyl |
| 90 | H | methyl | 2,5-dimethylphenylmethyl |
| 91 | H | methyl | methyl |
| 92 | H | methyl | 3-cyanophenylmethyl |
| 93 | H | methyl | 4-cyanophenylmethyl |
| 94 | H | phenyl | hydrogen |
| 95 | $-(CH_2)_4-$ | | hydrogen |
| 96 | $-(CH_2)_4-$ | | methyl |
| 97 | $-(CH_2)_4-$ | | phenylmethyl |
| 98 | H | H | 4-propionylphenylmethyl |

Other individual species of the compounds of Formula I that are of interest are the following, the symbols being those of Formula I:

| X | Y | Z |
|---|---|---|
| H | H | 3-fluorophenylmethyl |
| H | H | 3-fluorophenyl |
| H | H | 3-trifluoromethylphenyl |
| H | H | 3-pentafluoroethylphenylmethyl |
| H | H | 3-pentafluoroethylphenyl |
| H | H | 2-(methylamino)phenyl |
| | | 2-(methylamino)phenylmethyl |
| H | H | 2-(dimethylamino)phenyl |
| H | H | 2-(dimethylamino)phenylmethyl |

In addition to the lethality of those compounds with respect to those insect larvae, it was found that at sublethal dosages, they caused the insects to stop feeding, severely stunted their growth and development, and caused loss of body strength. In practice, these effects also enable control of pests, since if the pest is not killed directly by the compound of Formula I, the pest may die from secondary, exposure effects—i.e., desiccation, heat, etc.—and the pest may fall from the plant and die from exposure and/or starvation.

Compound 60, a typical species of the class defined by Formula I, also was found to be active with respect to the larvae of the black cutworm (*Agrotis ipsilon*), the cabbage looper (*Trichoplusia ni*), the tobacco budworm (*Heliothis virescens*), the Egyptian cotton leafworm (*Spodoptera littoralis*), German cockroaches (*Blatella germanica*) and adult houseflies (*Musca domestica*).

The intended use ordinarily will determine the way in which a compound of Formula I is to be applied to control pests. Thus, for controlling termites and other insects that attack wood, a suitable conventional formulation may be applied to the soil and/or surfaces of the wood to be protected, such formulations being described in more detail hereinafter. Plywood can be protected from insect pests by incorporating a compound of Formula I in the glue used to bond the plies together. Lumber, wood to be used for pilings or other maritime structures, telephone poles, fence posts and the like can be protected from termites, borers, shipworms (teredos) and the like by pressure treatment to impregnate the wood with a compound of Formula I. Bait formulations, using conventional lures and other components, together with a compound of Formula I, can be used to control many insects, such as the household and yard pests already mentioned, grasshoppers, crickets, ants, stored product pests, and the like. For fecal fly control, a compound of Formula I, appropriately formulated, can be applied to the feces, or, in the cases of at least some Formula I compounds, the pesticidally effective dosage is so much smaller than the dosage that would cause injury to the animal, that the compound can be included in the animal's feed and allowed to pass through the animal, giving control of insects feeding upon the evacuated feces.

For many applications, as has already been mentioned, the compound of Formula I can be conventionally formulated with a suitable inert carrier or surface-active agent, or both.

The term "carrier" as used herein means an inert or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, dimethyl sulfoxide, alcohols such as, for example, methanol, isopropyl alcohol, glycols; ketones such as, for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 5–80% by weight of the active compound and usually contain, in addition to the solid carrier, 3–10% by weight of a dispersing agent, 1–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 2–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

The method of applying a compound of this invention to control insects comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

The compounds of Formula I are known in the art, methods for their synthesis, and typical examples thereof being described in U.S. Pat. Nos. 4,118,561, 4,208,520 and 4,288,595.

We claim:

1. A method for protecting plants from insects which feed upon the foliage of plants, which comprises applying to the foliage of a plant to be protected an amount effective to either kill the insects or to cause the insects to stop feeding of a compound of the formula:

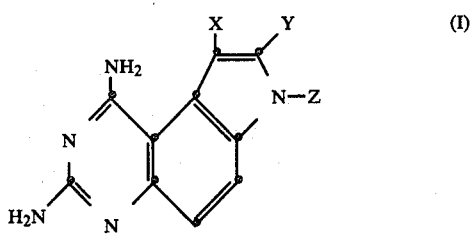

(I)

and acid addition salts thereof, wherein (A) X is hydrogen, Y is hydrogen, halogen, alkyl of from one to six carbon atoms, or phenyl, and
Z is one of
  (i) hydrogen;
  (ii) straight-chain or branched-chain alkyl of up to eight carbon atoms;
  (iii) a moiety R— or R—A—, wherein A is alkylene of from one to three carbon atoms with from one to two carbon atoms in the linking chain, and R is one of
    (a) phenyl; naphthalenyl;
    (b) phenyl substituted by alkanoyl of from two to six carbon atoms, aminocarbonyl, alkoxycarbonyl of from two to six carbon atoms, alkylsulfonyl of from one to three carbon atoms, or by from one to four substituents selected from halogen; nitro; amino; cyano; trifluoromethyl; trifluoromethoxy; or alkyl, alkoxy and alkylthio of from one to four carbon atoms each;
    (c) pyridinyl, thienyl, thiazolyl, isoxazolyl, quinolyl, pyrimidinyl, pyrazinyl, quinoxalinyl, or any of these substituted by from one to three substituents selected from halogen, nitro, trifluoromethyl, phenyl, and alkyl of from one to four carbon atoms; 1-benzo[b]-thienyl;
  (iv) cycloalkyl of from three to six carbon atoms;
  (v) phenylsulfonyl or phenylsulfonyl substituted by from one to three substituents selected from halogen, and alkyl of from one to four carbon atoms;
(B) X and Y together represent an alkylene moiety of from one to four carbon atoms, which may be substituted by one to three substituents selected from halogen, alkyl, alkoxy and alkylthio of from one to six carbon atoms, and Z is as defined in (A).

* * * * *